(12) United States Patent
Menko et al.

(10) Patent No.: US 9,273,133 B2
(45) Date of Patent: Mar. 1, 2016

(54) COMPOSITIONS AND METHODS FOR THE TREATMENT AND PREVENTION OF LENS FIBROTIC DISEASES

(75) Inventors: Allyn Sue Menko, Merion, PA (US); Mindy George-Weinstein, Wynnewood, PA (US); Janice L. Walker, Philadelphia, PA (US); Jacquelyn Gerhart, Wynnewood, PA (US)

(73) Assignees: Lankenau Institute for Medical Research, Wynnewood, PA (US); Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 13/132,745

(22) PCT Filed: Dec. 4, 2009

(86) PCT No.: PCT/US2009/066859
§ 371 (c)(1),
(2), (4) Date: Jul. 7, 2011

(87) PCT Pub. No.: WO2010/065920
PCT Pub. Date: Jun. 10, 2010

(65) Prior Publication Data
US 2011/0256054 A1 Oct. 20, 2011

Related U.S. Application Data

(60) Provisional application No. 61/119,750, filed on Dec. 4, 2008.

(51) Int. Cl.
*A61K 39/395* (2006.01)
*A61K 39/44* (2006.01)
*C07K 16/28* (2006.01)
*C07K 16/30* (2006.01)
*A61K 39/00* (2006.01)

(52) U.S. Cl.
CPC .................. *C07K 16/28* (2013.01); *C07K 16/30* (2013.01); *A61K 2039/505* (2013.01)

(58) Field of Classification Search
None
See application file for complete search history.

(56) References Cited

U.S. PATENT DOCUMENTS 6,180,357 B1 1/2001 Young et al.
2009/0297479 A1* 12/2009 Ariizumi et al. ............. 424/85.7

FOREIGN PATENT DOCUMENTS

WO 2004/0072117 8/2004
WO 2006/0128152 11/2006

OTHER PUBLICATIONS

Cornelison et al. Essential and separable roles for syndecans-3 and syndecan-4 in skeletal muscle development and regeneration. Genes & Development 18:2231-2236, 2004.*
Chen et al. Matrix contraction by dermal fibroblasts requires TGFbeta/ALK5, heparan sulfate containing proteoglycans and MEK/ERK: Insights into pathological scarring in chronic fibrotic disease.. Am J Pathol 2005, 167:1699-1711.*
Leask et al. Matrix contraction by dermal fibroblasts requires syndecan 4: Insights into pathological scarring in chronic fibrotic disease . The FASEB Journal. 2006;20:A1098). Abstract 688.8.*
Zammit et al. The Skeletal Muscle Satellite Cell: The Stem Cell That Came in From the Cold. J Histochem Cytochem 2006 54: 1177-1190.*
Cornelison et al. Syndecan-3 and Syndecan-4 Specifically Mark Skeletal Muscle Satellite Cells and Are Implicated in Satellite Cell Maintenance and Muscle Regeneration. Developmental Biology 239, 79-94 (2001).*
Wormstone et al. Hepatocyte Growth Factor Function and c-Met Expression in Human Lens Epithelial Cells Invest Ophthalmol Vis Sci. 2000;41:4216-4222.*
Tamaki et al. Identification of myogenic-endothelial progenitor cells in the interstitial spaces of skeletal muscle. J Cell Biol. 2002 May 13;157(4):571-7.*
Jejurikar and Kuzon. Satellite cell depletion in degenerative skeletal muscle. Apoptosis 2003; 8: 573-578.*
Gerhart, J., et al. "MyoD-positive myoblasts are present in mature fetal organs lacking skeletal muscle." J Cell Biol. 2001 Oct 29;155(3):381-92. Epub Oct. 29, 2001.
Srinivasan, Y., et al. "Lens-specific expression of transforming growth factor betel in transgenic mice causes anterior subcapsular cataracts." J Clin Invest. Feb. 1, 1998;101(3):625-34.
Gerhart, J., et al. "Tracking and ablating subpopulations of epiblast cells in the chick embryo." Biol Proced Online. Sep. 1, 2008;10:74-82.
Gerhart, J., et al. "Cells that express MyoD mRNA in the epiblast are stably committed to the skeletal muscle lineage." J Cell Biol. Aug. 13, 2007;178(4):649-60.
Gerhart, J., et al. "Epiblast cells that express MyoD recruit pluripotent cells to the skeletal muscle lineage." J Cell Biol. Mar. 1, 2004;164(5):739-46. Epub Feb. 23, 2004.
Strony, R., et al. "NeuroM and MyoD are expressed in separate subpopulations of cells in the pregastrulating epiblast." Gene Expr Patterns. Feb. 2005;5(3):387-95.
Iang, Q., et al. "EGF-Induced Cell Migration is Mediated by ERK and PI3K/AKT Pathways in Cultured Human Lens Epithelial Cells." J Ocular Pharma & Thera. Jan. 1, 2006;22(2):93-102.
Nagamoto, T., et al. "Alpha-smooth muscle actin expression in cultured lens epithelial cells." Invest Ophthalmol Vis Sci. Apr. 2000;41(5):1122-9.
Schmitt-Graff, A., et al. "Appearance of alpha-smooth muscle actin in human eye lens cells of anterior capsular cataract and in cultured bovine lens-forming cells." Differentiation. Apr. 1990;43(2):115-22.
Walker, J.L., et al. "Activation of SRC kinases signals induction of posterior capsule opacification." Invest Ophthalmol Vis Sci. May 2007;48(5):2214-23.
Zhou, J., et al. "SRC Kinase Activation Induces Formation of Lens Opacities Through a Pathway." Annual Meeting of the Association for Research in Vision and Opthamology. May 8, 2003; 2003.

(Continued)

*Primary Examiner* — Maher Haddad
(74) *Attorney, Agent, or Firm* — Robert C. Netter, Jr.; Dann, Dorfman, Herrell & Skillman

(57) ABSTRACT

Compositions and methods for treating fibrotic diseases are provided.

11 Claims, 11 Drawing Sheets

(56) References Cited

OTHER PUBLICATIONS

Zhou, J., et al. "Inhibition of SRC Family Kinases Blocks Formation of Cortical Cataracts in Cultured Chick Embryo Lenses." Annual Meeting of the Association for Research in Vision and Opthamology. May 10, 2002; 2002.

Wormstone, I.M., et al. "Identification of Signalling Pathways Involved in TGFB2 Induced Matrix Contraction of Human Lens Cells." Investigative Opthalmology & Visual Science.May 1, 2005;46(S).

Friedlander, M. "Fibrosis and diseases of the eye." J Clin Invest. Mar. 2007;117(3):576-86.

Gerhart, J., et al. "Noggin producing, MyoD-positive cells are crucial for eye development." Dev Biol. Dec. 1, 2009:336(1):30-41. Epub Sep. 22, 2009.

Walker, J., et al. "Unique precursors for the mesenchymal cells involved in injury response and fibrosis." Proc Natl Acad Sci U S A. Aug. 3, 2010;107(31):13730-5. Epub Jul. 15, 2010.

Wolff, I.M., et al. "Migration of Lens Epithelial Cells on the Posterior Lens Capsule is Blocked by Inhibition of Src Family Kinases." Invest Opthalmol Vis Sci. 2005;46:E-Abstract 2868.

Gerhart, J., et al. "MyoD-positive epiblast cells regulate skeletal muscle differentiation in the embryo." J Cell Biol. Oct. 23, 2006;175(2):283-92.

Zhang, G., et al. "Change of status in primary culture rabbits' lens epithelial cells." Int J Opthamol. Aug. 2008;8 (8):1563-1565. [Abstract].

* cited by examiner

COMPOSITIONS AND METHODS FOR THE TREATMENT AND PREVENTION OF LENS FIBROTIC DISEASES

This application is a §371 application of PCT/US2009/066859, filed Dec. 4, 2009, which claims priority under 35 U.S.C. §119(e) to U.S. Provisional Patent Application No. 61/119,750, filed on Dec. 4, 2008. The foregoing applications are incorporated by reference herein.

This invention was made with government support under Grant Nos. EY014258 and EY010577 awarded by the National Institutes of Health. The government has certain rights in the invention.

FIELD OF THE INVENTION

The present invention relates to the field of lens fibrotic disease. Specifically, compositions and methods for inhibiting, treating, and/or preventing fibrosis, particularly lens fibrotic disease, are disclosed.

BACKGROUND OF THE INVENTION

Several publications and patent documents are cited throughout the specification in order to describe the state of the art to which this invention pertains. Each of these citations is incorporated herein by reference as though set forth in full.

Myofibroblasts are the likely cause of lens fibrotic diseases that result in loss of vision, such as posterior capsule opacification (PCO) and anterior subcapsular cataract (ASC). PCO is a common complication of cataract surgery. The origin of myofibroblasts in ASC and PCO is unknown. Presently, there is no method that can be used to effectively block the development of lens fibrotic disease, such as PCO.

SUMMARY OF THE INVENTION

In accordance with the present invention, methods of inhibiting fibrotic disease, particularly lens fibrotic disease, are provided. In a particular embodiment, the methods comprise administering to the lens of a patient in need of such treatment a therapeutically effective amount of a composition comprising at least one skeletal muscle stem cell targeting molecule conjugated with at least one cytotoxic molecule, and at least one pharmaceutically acceptable carrier. In another embodiment, the lens fibrotic disease is posterior capsular opacification or anterior subcapsular cataract. In yet another embodiment, the composition of the instant invention is administered directly to the lens or the surrounding tissue.

According to another aspect of the instant invention, compositions for treating lens fibrotic disease are provided. In a particular embodiment, the compositions comprise at least one skeletal muscle stem cell targeting molecule conjugated with at least one cytotoxic molecule and at least one pharmaceutically acceptable carrier.

BRIEF DESCRIPTIONS OF THE DRAWING

FIGS. 1A and 1B provide images of skeletal muscle stem cells in the lens at Day 0 and Day 2, respectively, after mock cataract surgery on chicken lens capsular bags to induce posterior capsular opacification.

Figure 4:
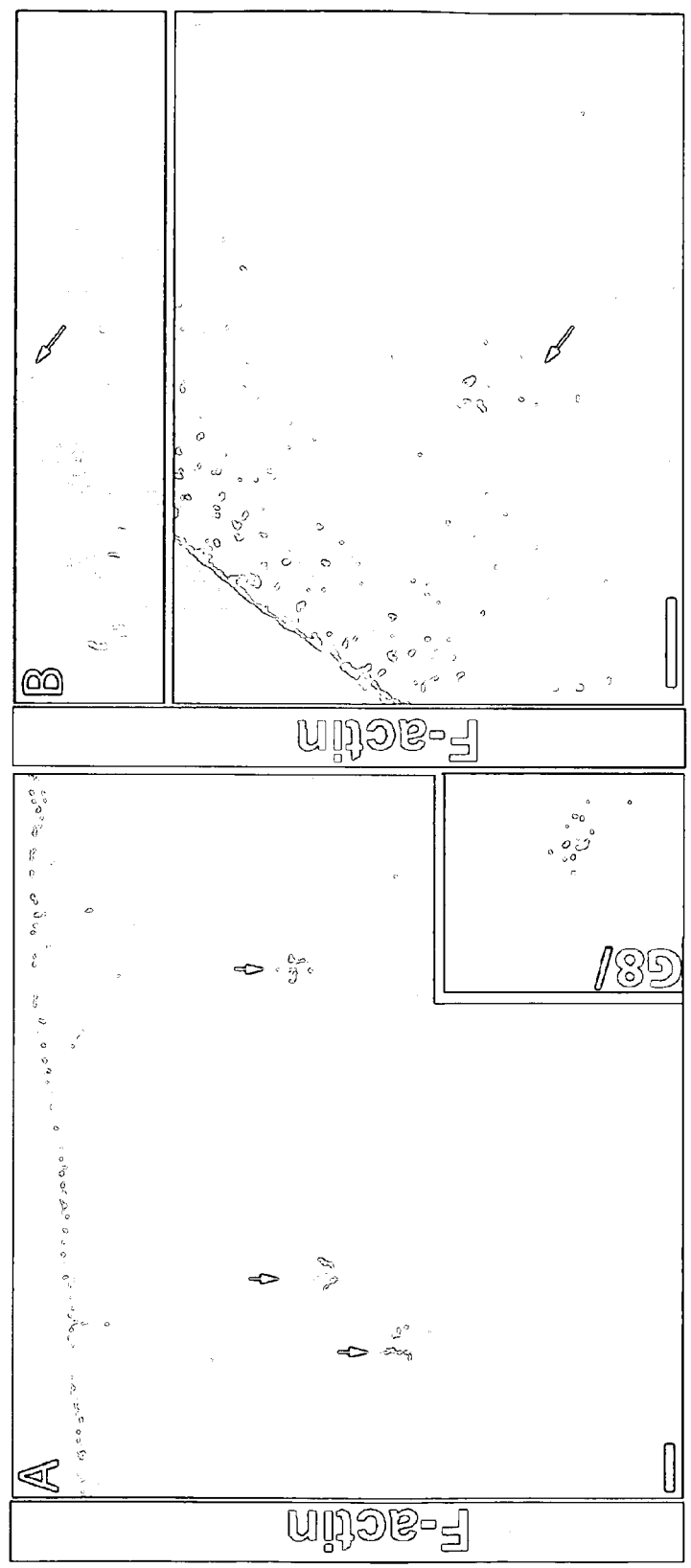

FIG. 4 provides images of a $G8^{pos}$ cell subpopulation that resides in niches within the lens epithelium. Lenses were fixed at E15 prior to preparation of epithelial explants, preserving the in situ localization $G8^{pos}$ cells. Explants were labeled with a mAb to the G8 antigen tagged with rhodamine-conjugated secondary antibody and co-stained for F-actin (Alexa Fluor-488 phalloidin) and nuclei (TO-PRO®-3, blue). Confocal imaging in a single optical plane digitally acquired as an x-y tile (FIG. 4A) showed $G8^{pos}$ cells localized to niches (arrows) nestled among the lens epithelial cells, at higher magnification in FIG. 4B, size bars 20 μm. Inset in FIG. 4A shows that lens epithelium-associated $G8^{pos}$ cells also expressed MyoD mRNA, detected with DNA dendrimers conjugated to a MyoD anti-sense oligonucleotide sequence tagged with Cy3, in explants fixed at T0 in culture; nuclei were counterstained with Hoechst dye. To further position the $G8^{pos}$ cell niches an orthogonal cut (top panel, FIG. 4B) was created from a Z-stack of consecutive 1 micron optical sections acquired apically to basally by scanning confocal imaging. The orthogonal cut was made along the horizontal line in the representative optical section (bottom panel, FIG. 4B). The $G8^{pos}$ niches were associated with the apical surfaces of lens epithelial cells (arrow, FIG. 4B).

Figure 5:
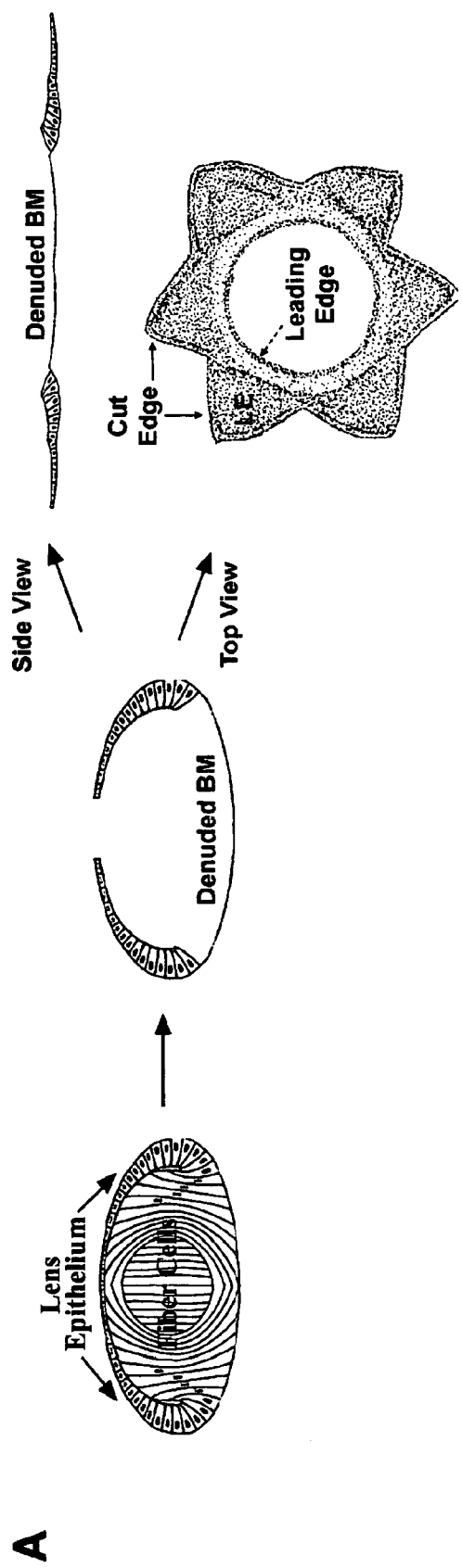
Figure 5:
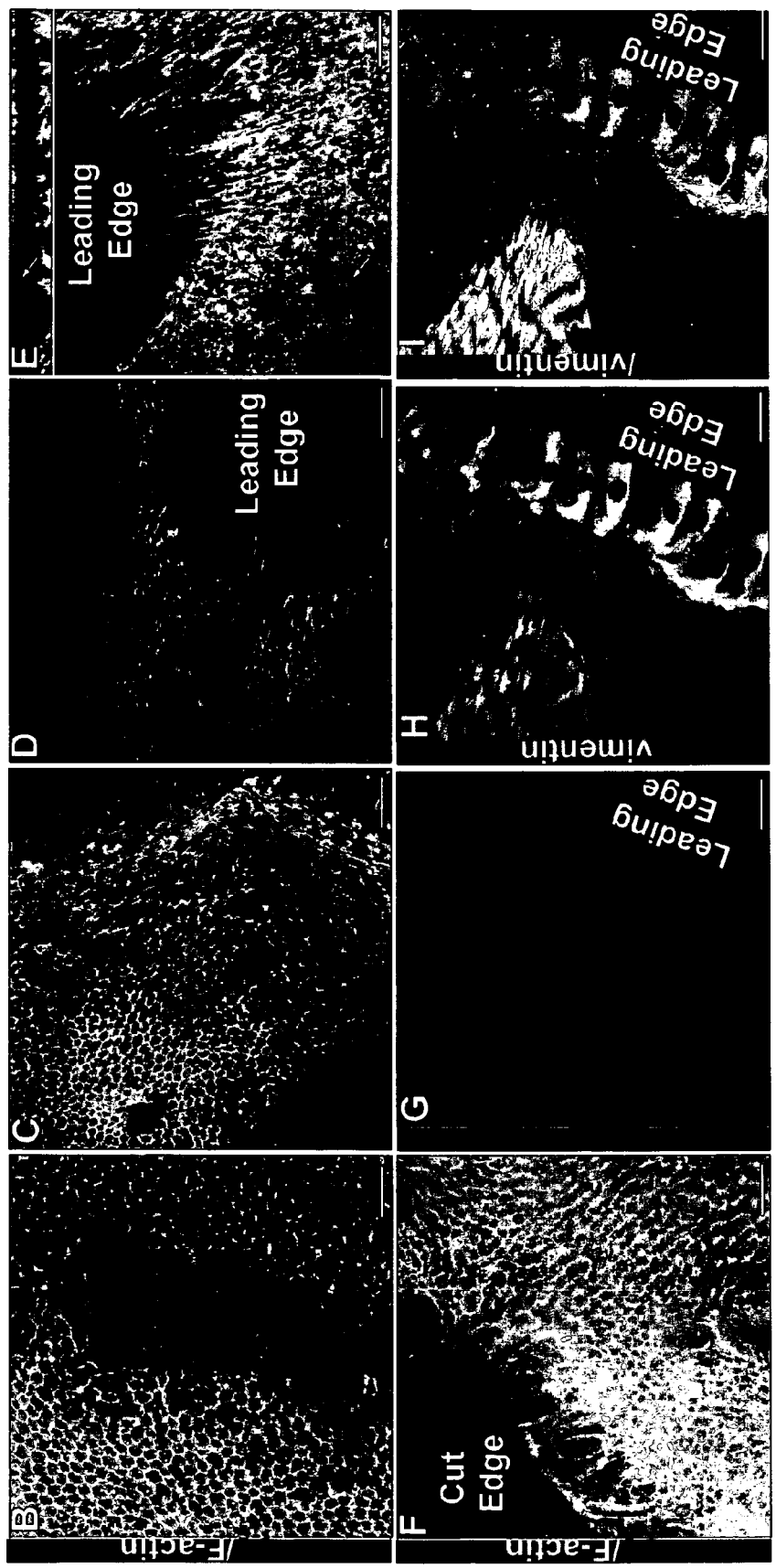

FIG. 5 shows that $G8^{pos}$ precursor cells expanded and migrated to wound edges in response to injury of epithelium. Mock cataract surgery was performed to prepare ex vivo wounded epithelial explants, modeled in (FIG. 5A). The fiber cell mass was removed from the lens capsule (a basement membrane, BM) creating a wounded leading edge in the lens epithelium (LE) where it had abutted the fiber cells. Cuts made in the anterior capsule to flatten the explant created a wounded cut edge. In FIGS. 5B-5F, the initial response of $G8^{pos}$ cells to injury was determined at 1 hour in culture by immunolabeling with G8 mAb. Staining of F-actin with Alexa Fluor 488-phalloidin outlined lens epithelial cells. Injury inflicted by mock cataract surgery induced emergence and expansion of the G8pos cell population (FIGS. 5B, 5C) and their migration toward wound edges, both leading (FIGS. 5D-5E) and cut (FIG. 5F) edges. Orthogonal cut (FIG. 5E, upper panel) through a confocal Z-stack at the position of the horizontal line (FIG. 5E, lower panel) showed that $G8^{pos}$ cells (arrow) migrated to the leading edge along apical surfaces of lens epithelial cells. FIGS. 5G-5I show that the mesenchymal phenotype of $G8^{pos}$ cells was demonstrated by double labeling for G8 and vimentin, overlayed in FIG. 5I. Size bar 20 μm.

Figure 6:
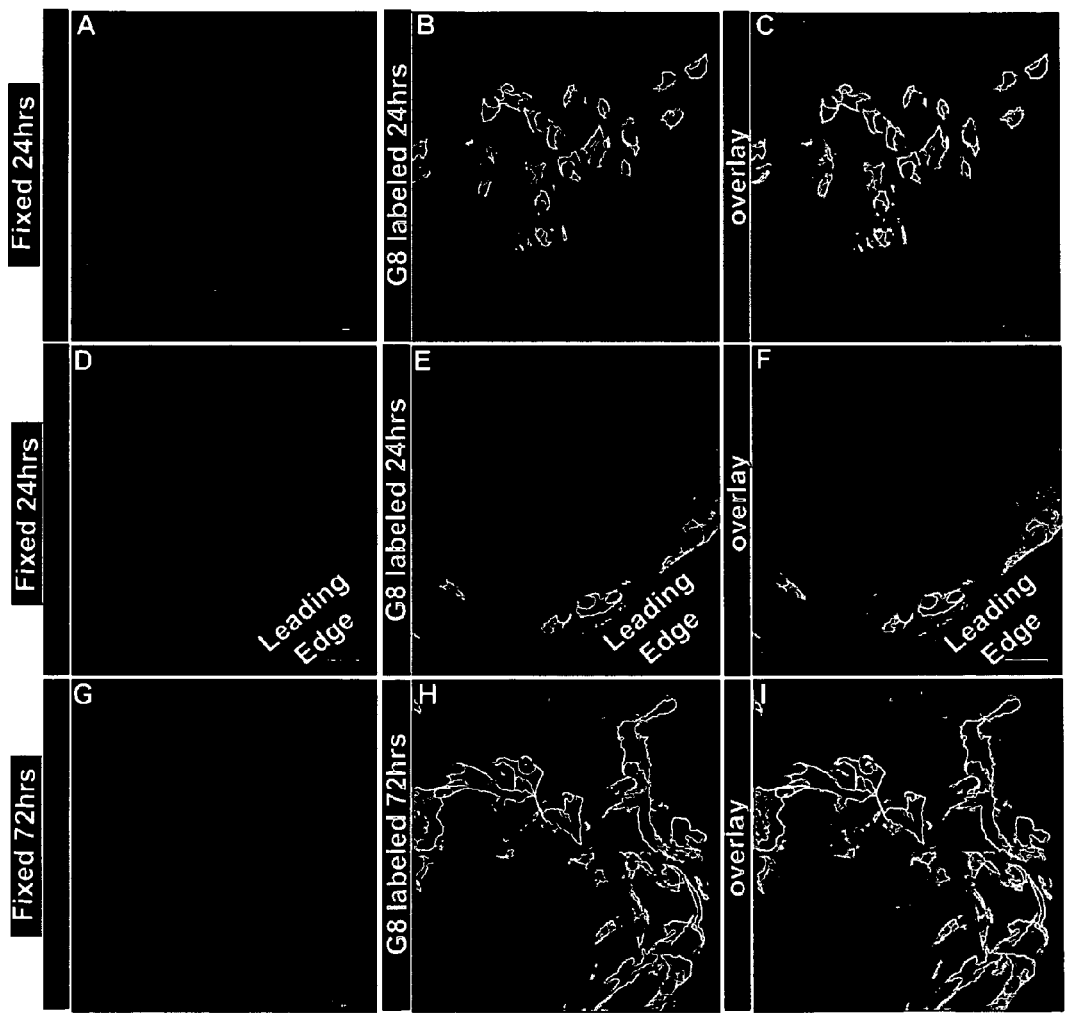

FIG. 6 provides tracking studies which show that $G8^{pos}$ cells responding to injury of the lens epithelium were progeny of $G8^{pos}$ cells present at the time of wounding. $G8^{pos}$ cells in lens epithelial ex vivo explants were tagged at T0 with G8 mAb and a rhodamine-conjugated secondary antibody. Explants with tagged G8 cells were incubated and the G8 cells tracked for 24 (FIGS. 6A-6F) or 72 (FIGS. 6G-6I) hours after the time of injury at which time they were fixed and labeled again with the G8 mAb, this time tagged with an Alexa-Fluor 488-conjugated secondary antibody. FIGS. 6A-6C and FIGS. 6G-6I are expanded niches, FIGS. 6D-6F cells at leading edge. All cells that labeled with the Alexa-Fluor 488-tagged G8 (FIGS. 6B, 6E, 6H) also were labeled with the tracked rhodamine-tagged G8 (FIGS. 6A, 6D, 6G), as seen in the overlays (FIGS. 6C, 6F, 6I). These results demonstrated that the $G8^{pos}$ cells that participated in healing of the lens epithelium were derived from the $G8^{pos}$ precursor cells present at the time of injury and did not include cells later recruited to the G8 lineage. Size bar 20 μm.

Figure 7:
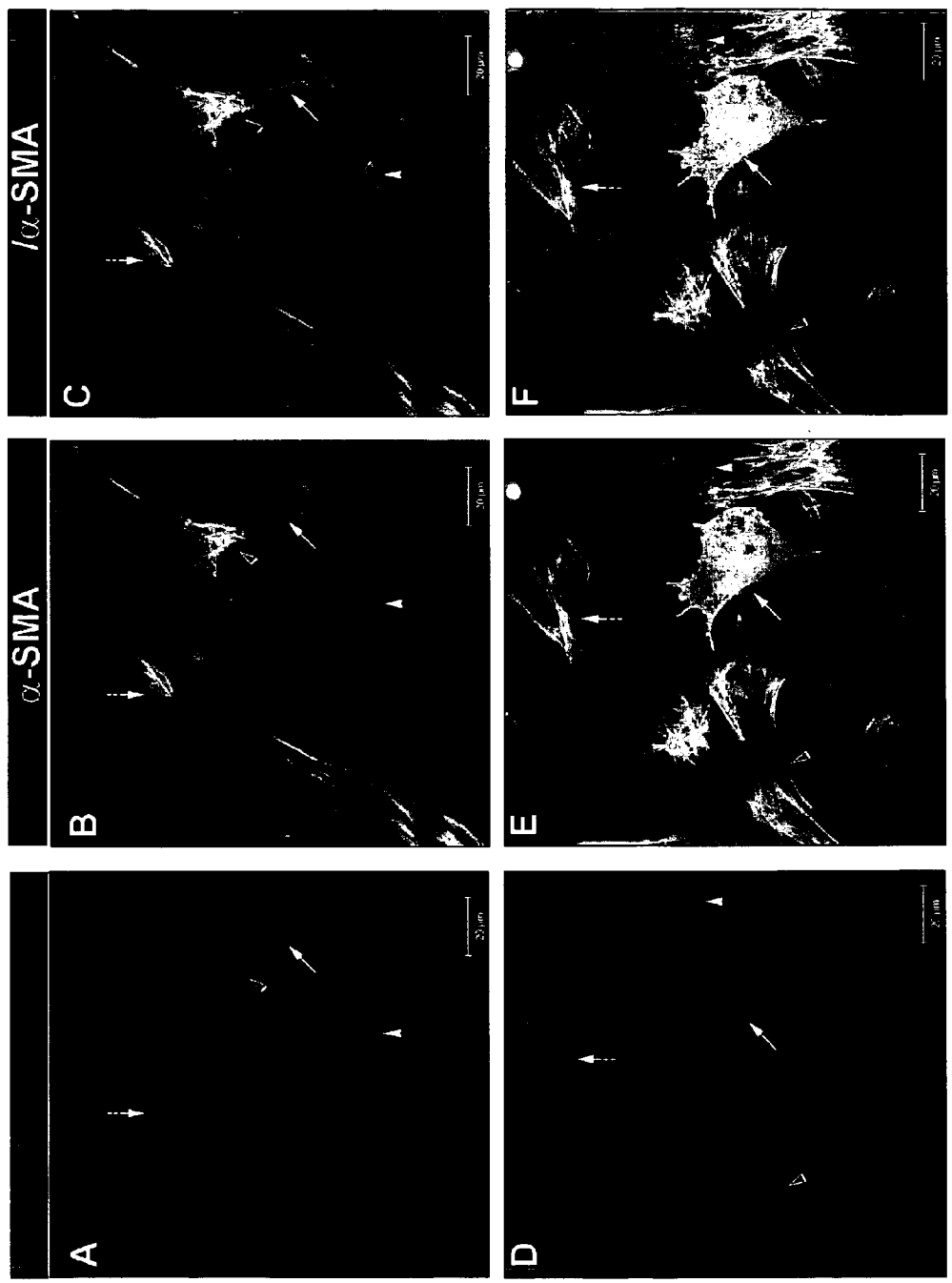
Figure 7:
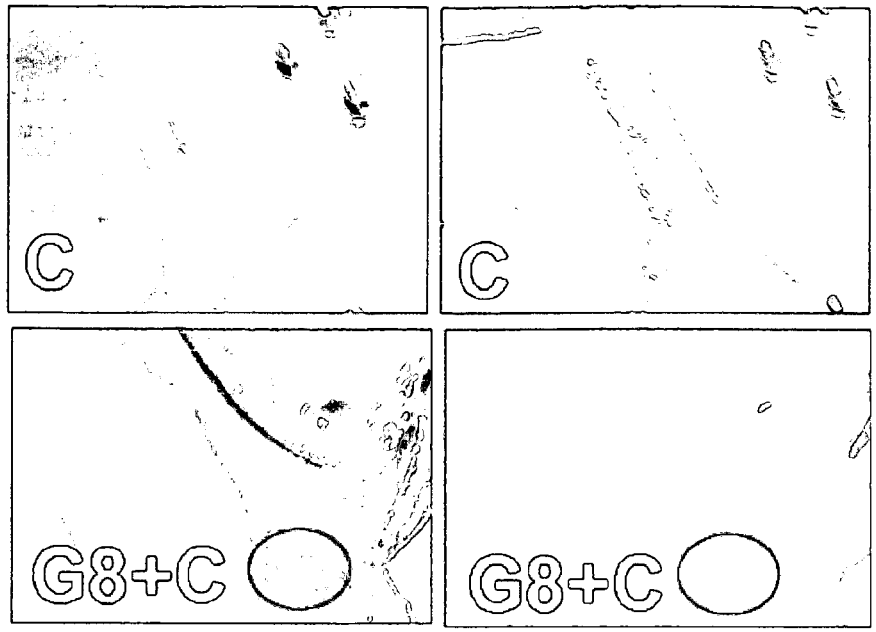
Figure 7:
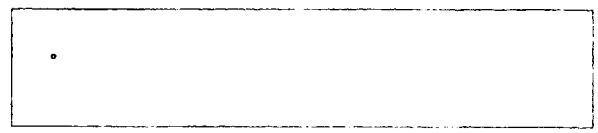

FIG. 7 shows that G8$^{pos}$ cells are myofibroblast precursors. Wounded lens epithelium cultured for 6 days (FIGS. 7A-7C) were double labeled for G8 antigen (FIG. 7A) and α-SMA (FIG. 7B), overlaid in FIG. 7C. Within colonies of G8$^{pos}$ cells there was a progression from G8$^{pos}$ cells to myofibroblasts: G8pos cells expressing little to no α-SMA (white arrowhead), G8$^{pos}$ cells expressing α-SMA not yet organized into stress fibers (arrow), G8$^{pos}$ cells with α-SMA containing stress fibers (open arrowhead), and myofibroblasts that had lost the G8 antigen (dashed arrow). Explants also were grown under conditions that permitted G8pos cells to migrate onto the rigid culture dish, promoting differentiation of G8 cells to myofibroblasts within 3 days (FIGS. 7D-7F), in the same progression noted above. Size bar 20 μm. FIGS. 7G, 7H show that G8$^{pos}$ cells were ablated in epithelial explants at culture day 1 by tagging them with G8 mAb and lysing them with complement, C. FIG. 7G provides a trypan blue uptake marks area of lysed cells (encircled area) in G8+C compared to C, confirmed by cell loss at 1D post ablation. FIG. 7H show epithelial explants exposed to G8+C, G8 alone, C alone, or untreated (U) at culture day 1, cultured another 5 days and immunoblotted for α-SMA and β-actin. Ablation of G8 cells blocked expression of α-SMA.

Figure 8A:
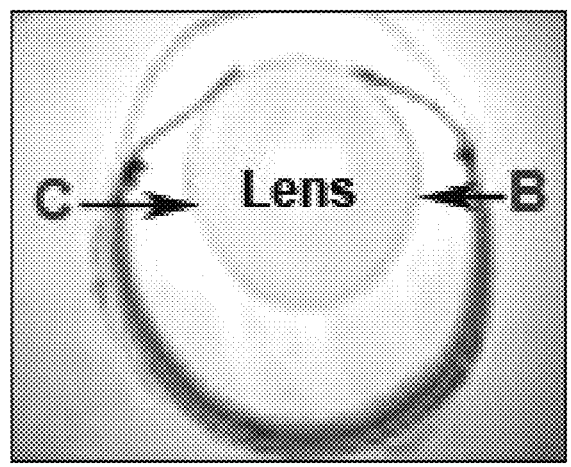
Figure 8B:
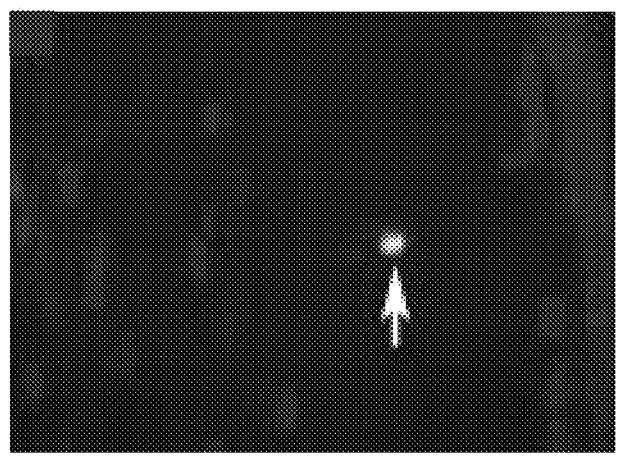
Figure 8C:
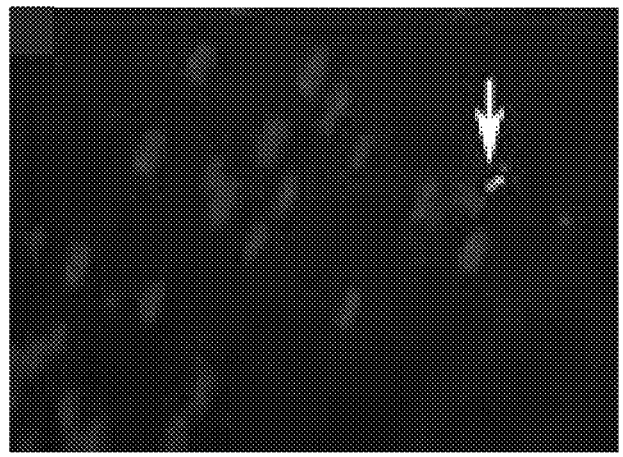
Figure 9:

FIG. 8A is an image of the eye of an adult mouse embedded in paraffin, sectioned, and stained with hematoxylin and eosin. The arrows indicate the areas shown at higher magnification in the fluorescence photomicrographs in FIGS. 8B and 8C. Cells labeled with the G8 antibody are shown with arrows in FIGS. 8B and 8C. Cell nuclei are also stained.

FIGS. 9A-9D are images of rhabdomyosarcomas cells stained for the presence of G8 antigen, alpha smooth muscle actin (SMA), myosin, and MyoD protein, respectively.

DETAILED DESCRIPTION OF THE INVENTION

The lens is presumed to consist of a single cell type, epithelial cells. Accordingly, it may be hypothesized that myofibroblasts within the lens develop from lens epithelial cells that undergo an epithelial to mesenchymal transition. This trans-differentiation can be identified by the expression of α-smooth muscle actin (α-SMA).

A model for lens fibrotic disease is provided herein in which cultured chick embryo lenses recapitulate the major features of the lens fibrotic disorder post capsular opacification, i.e., proliferation, migration across the posterior capsule, and expression of mesenchymal markers. This model was used to identify the cells responsible for causing fibrosis. In particular, skeletal muscle stem cells (skm stem cells), a newly identified population of cells in the lens that expresses MyoD mRNA and the G8 antigen, were determined to play a major role in the development of lens fibrotic disease.

As demonstrated hereinbelow, the lens contains a unique subpopulation of stem cells that express markers of the skeletal muscle lineage. These skm stem cells are present in niches within the equatorial epithelium. Upon injury, skm stem cells are activated to emerge from the epithelium and express α-smooth muscle actin (α-SMA). Skm stem cells are responsible for the expression of α-smooth muscle actin (α-SMA), a marker of myofibroblasts. These results indicate that the subpopulation of skm stem cells is the cause of fibrotic disease of the lens.

Posterior capsule opacification (PCO) is a disease that develops in 20-40% of patients following cataract surgery. Lens epithelial cells that are left behind following cataract surgery migrate onto the cleared posterior capsule of the lens. A subpopulation of cells that emerges from the epithelium is responsible for fibrotic changes that impair vision during the development of PCO. As demonstrated herein, the cells with myofibroblast-like properties originate from skeletal muscle stem cells embedded in the epithelium of the lens. Skeletal muscle stem cells within the lens can be identified based on their expression of the skeletal muscle specific transcription factor MyoD (e.g., MyoD mRNA) and the G8 antigen. Skeletal muscle stem cells may also express Noggin.

In accordance with the instant invention, methods of inhibiting, preventing, reducing the risk of, and/or treating fibrotic diseases/fibrosis, particularly ocular fibrotic diseases, are provided. In a particular embodiment, the methods of the instant invention inhibit fibrosis in an organ or tissue (e.g., in the heart, skin, intestine, lungs, liver, and/or kidney). In a particular embodiment, the methods comprise reducing and/or eliminating the skeletal muscle stem cells in the eye, particularly the lens. In a preferred embodiment, the ocular fibrotic disease is a lens fibrotic disease. Ocular fibrotic diseases include, without limitation, congenital ocular fibrosis syndrome, ocular allergic diseases (e.g., ocular allergic inflammation), fibrosis of the cornea, fibrosis of the trabecular meshwork, fibrosis of the retina, and lens fibrotic diseases. Lens fibrotic diseases include, without limitation, posterior capsule opacification and cataract (e.g., anterior subcapsular cataract).

Ablation of skeletal muscle stem cells can be achieved by various approaches. In a particular embodiment, the methods of the instant invention takes advantage of the fact that skeletal muscle stem cells possess different molecules (e.g., at the plasma membrane) than other cells, particularly lens epithelial cells. In a particular embodiment of the instant invention, the methods of inhibiting, preventing, reducing the risk of, and/or treating lens fibrotic disease comprise the administration of at least one molecule comprising at least one skeletal muscle stem cell targeting moiety optionally with (e.g., conjugated to) at least one cytotoxic molecule. The molecule(s) of the instant invention may be contained in at least one pharmaceutically acceptable carrier. In a particular embodiment, the targeting moiety is covalently linked to the cytotoxic molecule, optionally through a linking domain. In another embodiment, the cytotoxic molecule is attached to a molecule having specific affinity for the targeting moiety (e.g., an antibody which recognizes the G8 antibody). In yet another embodiment, the targeting moiety and cytotoxic molecule are not covalently linked. For example, the method of the instant invention may comprise the administration of the G8 antibody (a skm stem cell targeting molecule) and complement in a pharmaceutical composition or separate pharmaceutical compositions administered sequentially or concurrently.

Specific targeting of skeletal muscle stem cells can be achieved by specifically binding cell surface molecules, e.g., with ligands and/or antibodies, which are unique to skeletal muscle stem cells compared to lens epithelial cells. Cell surface targets for skeletal muscle stem cells include, without limitation, G8 antigen, syndecans (syndecans 1-4), c-Met (mesenchymal-epithelial transition factor; hepatocyte growth factor receptor (HGFR)), CD34, and M-cadherin. In a particular embodiment, the cell surface target is G8 antigen. Accordingly, the targeting moiety of the instant invention specifically binds a cell surface target of skeletal muscle stem cells to the general exclusion of other lens cells, e.g., lens epithelial cells.

Skeletal muscle stem cells can be eliminated/reduced by coupling the targeting moiety to reagents that induce cell death (e.g., a cytotoxic molecule). Cytotoxic molecules include, without limitation, complement (e.g., mouse, rat, rabbit, guinea pig, cow, horse, and human; e.g., blood/serum fractions containing complement; e.g., complement component(s)/protein(s); e.g., activators of complement), nanoparticles and nanotubes (e.g., heat sensitive carbon nanocrystals; see e.g., Chakravarty et al. (2008) PNAS 105:8697-8702) and Cho et al. (2008) Clin. Cancer Res., 14:1310-1316), cytoxic antibiotics (e.g., calicheamicin), cationic amphipathic lytic peptides (e.g., KLA (amino acid sequence: KLAKLAKKLAKLAK (SEQ ID NO: 2)) and PTP (prostate-specific membrane antigen-targeting peptide: CQKHHNYLC (SEQ ID NO: 3))), radionuclides, and toxins. Toxins can be derived from various sources, such as plants, bacteria, animals, and humans or be synthetic toxins (drugs), and include, without limitation, saprin, ricin (e.g., ricin A), abrin, ethidium bromide, diptheria toxin, Pseudomonas exotoxin, PE40, PE38, saporin, gelonin, RNAse, peptide nucleic acids (PNAs), ribosome inactivating protein (RIP) type-1 or type-2, pokeweed anti-viral protein (PAP), bryodin, momordin, chemotherapeutic agents, and bouganin. Radionuclides of the instant invention include, without limitation, positron-emitting isotopes and alpha-, beta-, gamma-, Auger- and low energy electron-emitters. In a particular embodiment, the radionuclides are alpha-emitters or auger-emitters. The radioisotopes include, without limitation: $^{13}N$, $^{18}F$, $^{32}P$, $^{64}Cu$, $^{66}Ga$, $^{67}Ga$, $^{68}Ga$, $^{67}Cu$, $^{77}Br$, $^{80m}Br$, $^{82}Rb$, $^{86}Y$, $^{90}Y$, $^{95}Ru$, $^{97}Ru$, $^{99m}Tc$, $^{103}Ru$, $^{105}Ru$, $^{111}In$, $^{113m}In$, $^{113}Sn$, $^{121m}Te$, $^{122m}Te$, $^{125m}Te$, $^{123}I$, $^{124}I$, $^{125}I$, $^{126}I$, $^{131}I$, $^{133}I$, $^{165}Tm$, $^{167}Tm$, $^{168}Tm$, $^{177}Lu$, $^{186}Re$, $^{188}Re$, $^{195m}Hg$, $^{211}At$, $^{212}Bi$, $^{213}Bi$, and $^{225}Ac$. In yet another embodiment, the radionuclide containing molecule can be administered with a radiosensitizer.

The present invention encompasses compositions comprising 1) at least one targeting moiety optionally with (e.g., conjugated to) at least one cytotoxin and 2) at least one pharmaceutically acceptable carrier. Such compositions may be administered, in a therapeutically effective amount, to a patient in need thereof for the treatment of a fibrotic disease, particularly lens fibrotic disease. Composition(s) of the instant invention may be contained within a kit.

The compositions of the present invention can be administered by any suitable route, for example, by injection (e.g., for local (direct, including intraocular lens) or systemic administration), oral, pulmonary, topical, nasal or other modes of administration. The composition may be administered by any suitable means, including parenteral, intramuscular, intravenous, intraarterial, intraperitoneal, subcutaneous, topical, inhalatory, transdermal, intraocular, intrapulmonary, intraareterial, intrarectal, intramuscular, and intranasal administration. In a preferred embodiment, the composition is administered directly to the eye, particularly the lens. In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., Tween 80, Polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, Pa. 18042) pages 1435 1712 which are herein incorporated by reference. The pharmaceutical composition of the present invention can be prepared, for example, in liquid form, or can be in dried powder form (e.g., lyophilized for later reconstitution).

In a particular embodiment, the compositions of the instant invention comprise eye drops, injectable solutions, or eye ointments. Injectable solutions can be directly injected into the lens or the adjacent tissues using a fine needle. The composition may also be administered to the eye via a contact lens or, more preferably, an intraocular lens (e.g., the intraocular lens used in the cataract surgery). The lens may be coated and/or embedded with the composition or may be soaked in the composition.

In yet another embodiment, the compositions of the instant invention can be administered at the time of cataract surgery, after cataract surgery, or prior to cataract surgery in order to prevent fibrosis (e.g., the fibrosis that causes PCO). In still another embodiment, the compositions of the instant invention can be injected directly into the lens capsule capsular bag following removal of the fiber cell mass. Since the lens is avascular, the molecules of the instant invention (e.g., coupled antibodies) are not expected to enter the systemic circulation.

The procedures described herein are used to specifically target and eliminate/reduce skeletal muscle stem cells in the lens epithelium. However, the methods of the instant invention could be used to ablate skeletal muscle stem cells in other tissues to treat, inhibit, and/or prevent other diseases and disorders associated with aberrant behavior and/or amounts of skeletal muscle stem cells and/or aberrant fibrosis. Such diseases and disorders include, for example, scar tissue formation (e.g., of the skin, heart, or liver).

DEFINITIONS

The following definitions are provided to facilitate an understanding of the present invention:

The term "fibrosis" refers to any excess production or deposition of extracellular matrix proteins. Fibrosis includes any abnormal processing of fibrous tissue, or fibroid or fibrous degeneration. Fibrosis can result from various injuries or diseases. The term "ocular fibrosis" refers to fibrosis affecting the eye or some portion thereof.

An "antibody" or "antibody molecule" is any immunoglobulin, including antibodies and fragments thereof, that binds to a specific antigen. The term includes polyclonal, monoclonal, chimeric, single domain (Dab) and bispecific antibodies. As used herein, antibody or antibody molecule contemplates recombinantly generated intact immunoglobulin molecules and immunologically active portions of an immunoglobulin molecule such as, without limitation: Fab, Fab', F(ab')$_2$, F(v), scFv, scFv$_2$, scFv-Fc, minibody, diabody, tetrabody, single variable domain (e.g., variable heavy domain, variable light domain), and bispecific. Dabs can be composed of a single variable light or heavy chain domain. The instant invention also encompasses Affibody® molecules (Affibody, Bromma, Sweden) and peptabodies (Terskikh et al. (1997) PNAS 94:1663-1668). In a certain embodiment of the invention, the variable light domain and/or variable heavy domain specific for target molecule on skeletal muscle stem cells are inserted into the backbone of the above mentioned antibody constructs. Methods for recombinantly producing antibodies are well-known in the art. "Fv" is an antibody fragment which contains an antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although often at a lower affinity than the entire binding site.

"Single-chain Fv" or "scFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. The term "diabodies" refers to small antibody fragments with two antigen-binding sites, which fragments comprise a heavy-chain variable domain ($V_H$) connected to a light-chain variable domain ($V_L$) on the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Holliger et al., (1993) Proc. Natl. Acad. Sci. USA, 90: 6444-6448. In yet another embodiment, the antibody is humanized.

With respect to antibodies, the term "immunologically specific" refers to antibodies that bind to one or more epitopes of a protein or compound of interest, but which do not substantially recognize and bind other molecules in a sample containing a mixed population of antigenic biological molecules. The term "specifically binds" refers to the binding of a polypeptide or compound of interest to a target polypeptide or compound while not substantially recognizing and binding other molecules in a sample containing a mixed population of biological molecules. For example, a "specific binding pair" comprises a specific binding member and a binding partner which have a particular specificity for each other and which in normal conditions bind to each other in preference to other molecules.

The term "conjugated" refers to the joining by covalent or noncovalent means of two molecules or compounds of the invention. The molecules may be joined by a linker domain.

The term "linker domain" refers to a chemical moiety comprising a covalent bond or a chain of atoms that covalently attaches the targeting moiety to the cytotoxin. In a particular embodiment, the linker may contain from 0 (i.e., a bond) to about 500 atoms, about 1 to about 100 atoms, or about 1 to about 50 atoms. Exemplary linkers may comprise at least one optionally substituted; saturated or unsaturated; linear, branched or cyclic alkyl, alkenyl, or aryl group. The linker may also be a polypeptide (e.g., from about 1 to about 20 amino acids).

The term "radiosensitizer", as used herein, is defined as a molecule administered to animals in therapeutically effective amounts to increase the sensitivity of the cells to radiation. Radiosensitizers are known to increase the sensitivity of cells to the toxic effects of radiation. Radiosensitizers include, without limitation, 2-nitroimidazole compounds, and benzotriazine dioxide compounds, halogenated pyrimidines, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), antimicrobial, bulking substance (e.g., lactose, mannitol), excipient, auxilliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

The following examples provide illustrative methods of practicing the instant invention, and are not intended to limit the scope of the invention in any way.

Example 1

Figures 1A, 1B:
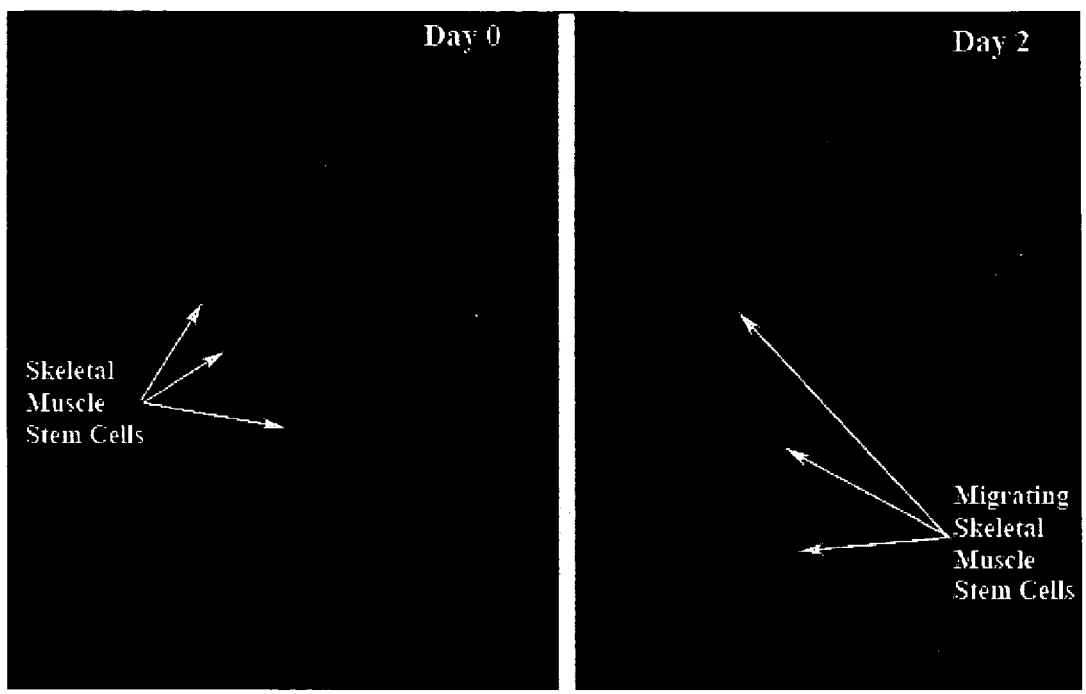
Figure 3:
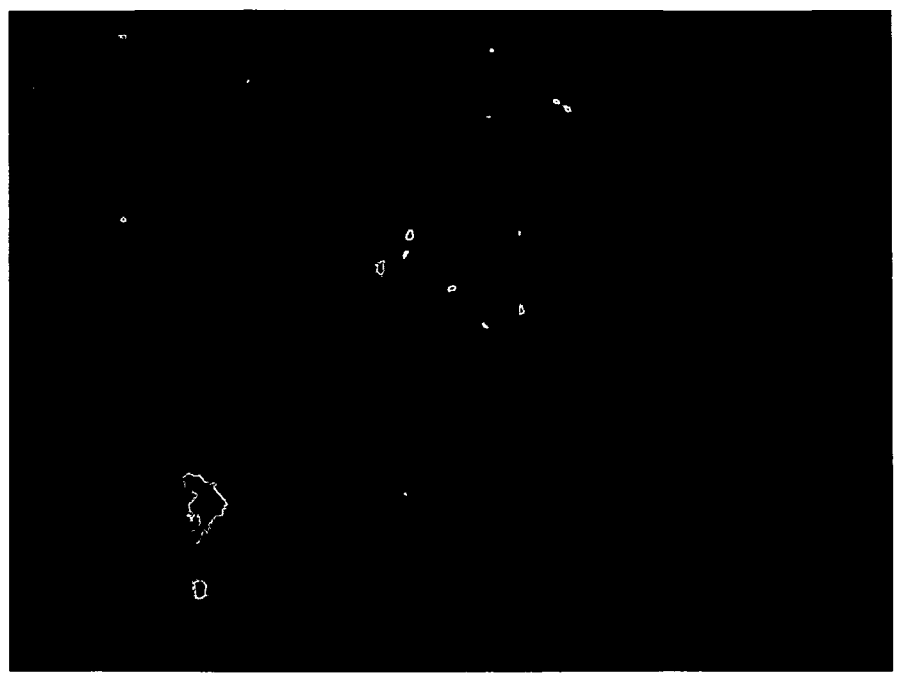
FIG. 3 is an image of G8 and MyoD mRNA labeled mouse lens cells.

After mock cataract surgery, chick lens capsular bags were pinned to a culture dish as previously described (Walker et al. (2007) Invest. Ophthalmol. Vis. Sci., 48:2214-23). Skeletal muscle stem cells (skm stem cells) were identified by immunofluorescence localization of the G8 antigen (FIG. 1), in situ hybridization for MyoD mRNA (FIG. 3), and confocal and epifluorescence microscopy. G8 antibody recognizes a surface antigen specifically expressed in cells that express MyoD mRNA in the chick embryo and fetus (Gerhart et al. (2001) J. Cell Biol., 155:381-391; Gerhart et al. (2004) J. Cell Biol., 164:739-746; Strony et al. (2005) Gene Expr. Patterns, 5:387-395) and adult mouse tissue (FIG. 3). Messenger RNAs for MyoD were detected with DNA dendrimers (see, e.g., Gerhart et al. (2004) Biol. Proced. Online, 6:149-156) conjugated with Cy3 and the following antisense oligonucleotide sequence: chicken MyoD, 5'-TTCTCAAGAGCAAATACT-CACCATTTGGTGATTCCGTGTAGTA-3' (L34006; Dechesne et al. (1994) Mol. Cell. Biol., 14:5474-5486). Fluorescent dendrimers were obtained from Genisphere, Inc. (Hatfield, Pa.). Double labeling with dendrimers and antibodies was performed as previously described Gerhart et al. (2001) J. Cell Biol., 155:381-391; Gerhart et al. (2004) J. Cell Biol., 164:739-746; Strony et al. (2005) Gene Expr. Patterns, 5:387-395; Gerhart et al. (2004) Biol. Proced. Online, 6:149-156).

Figure 2A:
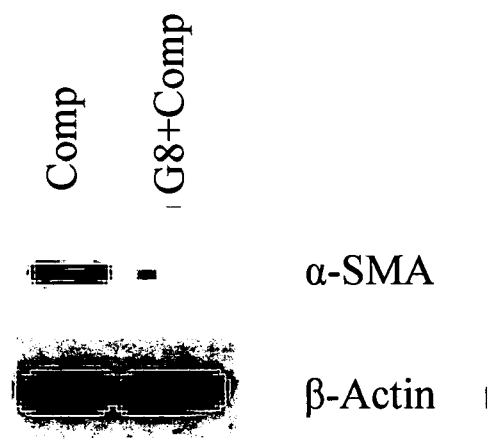
FIG. 2A is an image of a Western blot of α-smooth muscle actin and β-actin from posterior capsular opacification induced lenses (1 day) cultured in either complement alone or complement with G8 antibody.
Figure 2B:
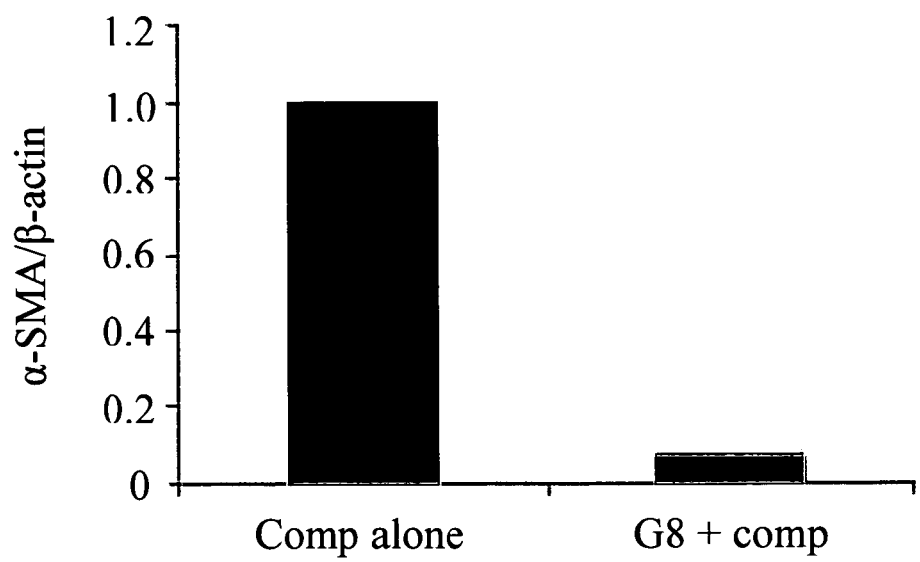
FIG. 2B is a graph of the signal intensity ratio of the Western blot in FIG. 2A.

Ablation of skm stem cells in day 1 PCO cultures was achieved by lysing cells labeled with the G8 antibody (see, e.g., Gerhart et al. (2001) J. Cell Biol., 155:381-391; Gerhart et al. (2004) J. Cell Biol., 164:739-746; Strony et al. (2005) Gene Exp. Patterns, 5:387-395; Gerhart et al. (2007) J. Cell Biol., 178:649-660; Gerhart et al. (2006) J. Cell Biol., 175: 283-292; Gerhart et al. (2008) Biol. Proc. Online, 10:74-82) by incubation in complement (FIG. 2). More specifically, the lenses were incubated with the G8 antibody diluted 1:20 in Hanks' buffered saline containing 0.1% bovine serum albumen (BSA) for one hour at 37°, washed, then incubated in baby rabbit complement (Cedarlane Laboratories, Burlington, N.C.) diluted 1:40 in Hanks' buffered saline containing 0.1% BSA at room temperature for 30 minutes. Expression of α-SMA was determined by Western blot analysis (FIG. 2).

A subpopulation of G8/MyoD mRNA positive skm stem cells were detected within a niche located in the equatorial zone (EQ) of the lens nestled among the lens epithelial cells. This finding demonstrates for the first time that there is a population of cells within the lens epithelium with stem cell properties and a phenotype distinct from lens epithelial cells. Upon injury induced by mock cataract surgery, skm cells quickly emerge from their niche with a mesenchymal morphology. These skm stem cells crawl over the top of the cuboidal lens epithelial cell monolayer and migrate to the leading edge of the collectively migrating epithelial cell sheet. Ablation of skm stem cells suppresses the expression of α-SMA expression in posterior capsular opacification cultures.

Skeletal muscle stem cells were also identified by immunofluorescence localization of the G8 antigen, in situ hybridization for MyoD mRNA, and epifluorescence microscopy (FIG. 3). Accordingly, it is evident that the presence of skeletal muscle stem cells in lenses is not limited to chickens as skm stem cells are also present in other animals including mammals.

Example 2

Mesenchymal cells play a central role in epithelial wound healing, fibrosis and cancer (Radisky et al. (2007) J. Cell Biochem., 101:830-9; Eyden, B. (2008) J. Cell Mol. Med., 12:22-37; Polyak et al. (2009) Nat. Rev. Cancer 9:265-73). The emergence of cells with a mesenchymal phenotype within an epithelial sheet is thought to result primarily from a transformation of endogenous epithelial cells, commonly referred to as an epithelial to mesenchymal transition (EMT) (Baum et al. (2008) Semin. Cell Dev. Biol., 19:294-308; Lee et al. (2006) J. Cell Biol., 172:973-81). In this study, the possibility that epithelia contain a subpopulation of mesenchymal precursor cells that function in epithelial wound healing and that can be signaled to differentiate into myofibroblasts was investigated. The model for these studies is an ex vivo culture system originally developed to study the lens fibrotic disease known as Posterior Capsule Opacification (PCO) (Walker et al. (2007) Invest. Ophthalmol. Vis. Sci., 48:2214-23). With this culture model it is possible to follow the response of an intact epithelium to a clinically relevant wounding within a native microenvironment. Wounding of the epithelium is the result of mock cataract surgery in embryonic day 15 chick lenses. This microsurgical procedure involves removal of the lens fiber cell mass from within the lens capsule, a thick basement membrane that surrounds the entire lens, which leaves the posterior aspects of the lens capsule denuded of cells (diagrammed in FIG. 5A). The lens epithelium remains intact and attached to the capsule with its principal wound edge bordering the area where the fiber cells had been attached (leading edge, FIG. 5A). By making a few cuts in its anterior regions, creating additional wound edges (cut edge, FIG. 5A), the tissue is flattened, pinned to the culture dish cell side up and cultured as an ex vivo explant (modeled in FIG. 5A). This approach makes it possible to follow the response of the wounded epithelium to injury using high resolution confocal microscopy. The epithelial cells in this wound model quickly begin a collective migration across the denuded basement membrane capsule into the wounded area and the wound is filled with epithelial cells within a few days in culture (Walker et al. (2007) Invest. Ophthalmol. Vis. Sci., 48:2214-23). Only after the wound healing process is completed is the expression of molecular markers associated with the emergence of myofibroblasts detected biochemically (Walker et al. (2007) Invest. Ophthalmol. Vis. Sci., 48:2214-23), demonstrating that in this ex vivo model the development of fibrotic-disease is principally a post migratory and post-wound closure event.

The hypotheses examined in this study were: 1) that a subpopulation of mesenchymal precursors was present among the epithelial cells of the mature lens, 2) that these cells could be activated upon injury to modulate the wound healing process, and 3) that the progeny of these cells have the potential to become myofibroblasts, a phenotype associated with the development of fibrotic disease. The cell type investigated as a candidate for the mesenchymal precursor cell in the lens injury model is identified by its expression of the cell surface antigen G8. Cells that label with the G8 monoclonal antibody (mAb) are a subpopulation of the epiblast, a tissue that gives rise to all three germ layers of the embryo (Bellairs, R. (1986) Anat Embryol (Berl) 174:1-14). These $G8^{pos}$ cells also express mRNA for the myogenic transcription factor myoD (George-Weinstein, et al. (1996) Dev. Biol., 173:279-91; Gerhart et al. (2000) J. Cell. Biol., 149:825-34). During development most of the $G8^{pos}/MyoD^{pos}$ epiblast cells become integrated into the somites where their function is to regulate muscle differentiation (Gerhart et al. (2006) J. Cell. Biol., 175:283-92); however, $G8^{pos}/MyoD^{pos}$ epiblast cells have myogenic potential themselves when isolated and grown in a culture dish (Gerhart et al. (2001) J. Cell. Biol., 155:381-92; Strony et al. (2005) Gene Expr. Patterns, 5:387-95; Gerhart et al. (2004) J. Cell. Biol., 164:739-46). Interestingly, subpopulations of both G8 antigen and MyoD expressing cells also have been detected amongst the cells of non-muscle tissues (Gerhart et al. (2001) J. Cell. Biol., 155:381-92; Asakura et al. (1995) Dev. Biol., 171:386-98; Chen et al. (2005) Genesis 41:116-21; Grounds et al. (1992) Exp. Cell. Res., 198:357-61), including the embryonic lens (E5, Gerhart et al. (2009) Developmental Biology 336:30-41), but their function in these tissues is not known.

Materials and Methods

Ex Vivo Epithelial Explant Preparation

To prepare ex vivo epithelial explants, lenses were removed from embryonic day (E)15 chick embryo (Truslow Farms, Chestertown, Md.) eyes by dissection (Walker et al. (2007) Invest. Ophthalmol. Vis. Sci., 48:2214-23). Then an incision was made in the anterior lens capsule, the thick basement membrane that surrounds the lens, from which the lens fiber cell mass was removed by hydroelution. This process, in which the lens epithelium remains tightly adherent to the capsule, mimics cataract surgery. The principle wound edge (leading edge) of the epithelium, borders the area where the fiber cells had been attached (model, FIG. 5A). Cuts were made in the anterior region of this tissue, creating additional wound edges that allowed the explants to be flattened and pinned to the culture dish cell side up (FIG. 5A). The response of the lens epithelium to wounding within their native microenvironment was followed by microscopic imaging. The ex vivo epithelial explants were cultured in Media 199 (Invitrogen) containing 1% pen-strep (Mediatech-Cellgro, Manassas, Va.), 1% L-glutamine (Mediatech-Cellgro, Manassas, Va.) with or without 10% fetal calf serum (Invitrogen) as specified. In experiments designed to preserve the position of the $G8^{pos}$ cells as they occur in vivo, lenses were fixed for 10 minutes in 3.7% formaldehyde prior to preparing the epithelial explants.

Immunofluorescence and In Situ Hybridization

For immunofluoresence studies, epithelial explants were immunostained as described previously (Walker et al. (2007)

Invest. Ophthalmol. Vis. Sci., 48:2214-23). Briefly, explants were fixed in 3.7% formaldehyde in PBS and permeabilized in 0.25% Triton X-100 in PBS before immunostaining. Cells were incubated with primary antiserum followed by rhodamine—(Jackson Laboratories, West Chester, Pa. and Millipore Corp., Bedford, Mass.), fluorescein—(Jackson Laboratories, West Chester, Pa.) or Alexa Fluor 488-(Invitrogen-Molecular Probes; Eugene, Oreg.) conjugated secondary antibodies. The following primary antibodies were used for the immunofluorescence studies, G8 mAb (Gerhart et al. (2001) J. Cell. Biol., 155:381-92) vimentin (polyclonal) antibody a generous gift from Paul FitzGerald (University of California, Davis, Calif.) and fluorescein (FITC)-conjugated α-SMA mAb (Sigma, St. Louis, Mo.). Some explants were counterstained with Alexa Fluor 488-conjugated phalloidin, which binds filamentous actin, and TO-PRO® 3, a nuclear stain (Invitrogen-Molecular Probes; Eugene, Oreg.). All immunostained samples were examined with a confocal microscope (LSM 510; Carl Zeiss, Oberkochen, Germany) except those that were also processed for in situ hybridization. Either single images or Z-stacks were collected and analyzed; the data presented represent single optical planes or orthogonal sections imaged from the apical to basal direction.

For in situ hybridization studies mRNAs for MyoD were detected with DNA dendrimers conjugated with Cy3 and the following antisense oligonucleotide sequence: chicken MyoD, 5'-TTCTCAAGAGCAAATACTCACCATTTG-GTGA TTCCGTGTAGTA-3' (SEQ ID NO: 1) (Genisphere, Inc., Hatfield, Pa.) (Gerhart et al. (2006) J. Cell. Biol., 175: 283-92; Gerhart et al. (2004) Biol. Proced. Online, 6:149-156). Explants were double labeled for the G8 antigen and MyoD mRNA, and counterstained with Hoechst as previously described (Gerhart et al. (2001) J. Cell. Biol., 155:381-92) and examined with an epifluoresence microscope (Eclipse E800, Nikon). Images were captured with a video camera (Evolution QE; Media Cybernetics) and Image-Pro Plus software (Phase 3 Imaging Systems).

Cell Tracking

G8 cells were labeled for tracking according to a previously described procedure (Gerhart et al. (2006) J. Cell. Biol., 175:283-92). Briefly, the lens ex vivo epithelial explants were incubated at T0 in Media 199 containing the G8 mAb (1:40) for 45 minutes at room temperature, rinsed in Media 199, and then incubated in rhodamine-conjugated IgM antibody (Millipore Corp., Bedford, Mass.) for 30 minutes at room temperature. The labeled explants were rinsed in Media 199, placed in serum free media (SFM: Media 199 containing 1% Pen strep and L-glutamine) and incubated at 37° C. After 24 hours or 72 hours in culture the epithelial explants were fixed in 3.7% formaldehyde. To determine if G8$^{pos}$ cells that responded to epithelial wound healing 24 or 72 hours post-injury were indeed progeny of G8$^{pos}$ cells present at T0 the fixed explants were labeled again with the G8 mAb (1:40) this time followed by an IgM secondary antibody conjugated to Alexa Fluor 488 (Invitrogen-Molecular Probes, Eugene, Oreg.). Previous fate mapping studies in which G8$^{pos}$ cells are tracked from the epiblast to embryonic tissues demonstrate that G8 mAb that tags G8pos cells in the epiblast remains associated with these cells throughout the study and does not transfer to surrounding cells (Gerhart et al. (2006) J. Cell. Biol., 175:283-92).

G8$^{pos}$ Cell Ablation in Epithelial Cell Explants

G8$^{pos}$ cell ablation in epithelial explants followed a procedure previously described for ablation of G8$^{pos}$ cells within the epiblast of the chick embryo (Gerhart et al. (2006) J. Cell. Biol., 175:283-92). For these studies ex vivo lens epithelial explants were prepared in SFM. On culture day 1, epithelial explants were incubated with G8 antigen (1:20) diluted in Hanks Buffered Saline for 1 hour at 37° C. followed by incubation in baby rabbit complement (1:40; Cedar Lane, Inc, Burlington, Ontario, Canada) diluted in Hanks buffered saline containing 0.1% BSA for 30 minutes at room temperature. Baby rabbit complement was prepared according to manufactures protocol (Cedar Lane, Inc, Burlington, Ontario, Canada). Control explants were left untreated or incubated with G8 mAb or complement alone. After treatment, explants were rinsed and incubated with SFM. The presence of lysed G8 cells was determined immediately after treatment by incubating the ex vivo epithelial explants in 0.2% trypan blue in PBS for 15 minutes at 37° C. and visualized with a dissecting microscope (SMZ800; Nikon, Tokyo, Japan) and a Nikon Digital Sight DS-Fi1 camera and the images captured using Nikon NIS-Elements imaging software.

Western Blot Analysis

On Day 6, epithelial explants were extracted and lysed in OGT buffer (44.4 mM n-Octyl β-D glucopyranoside, 1% Triton X-100, 100 mM NaCl, 1 mM MgCl$_2$, 5 mM EDTA, 10 mM imidazole) containing a protease inhibitor cocktail (Sigma, St. Louis, Mo.). Protein concentrations were determined with the BCA assay (Pierce, Rockford, Ill.). Proteins were separated on Tris-glycine gels (Novex, San Diego, Calif.), electrophoretically transferred to membrane (Immobilon-P; Millipore Corp., Bedford, Mass.), and immunoblotted. For detection, ECL reagent (Amersham Life Sciences, Arlington Heights, Ill.) was used. All gels were run under reducing conditions. Antibodies used for western blotting included β-actin and α-smooth muscle actin (Sigma, St Louis, Mo.).

Results

It was identified that G8$^{pos}$ cells were present in mature lenses (E15) and determined their localization, in situ, focusing on their association with the lens epithelium. In order to preserve the position of G8$^{pos}$ cells as exists in vivo, lenses were fixed prior to the preparation of lens epithelial explants. G8$^{pos}$ cells within the explants were labeled with a mAb to the G8 antigen followed by a rhodamine-conjugated secondary antibody. The cultures were co-stained with fluorescein-conjugated phalloidin to tag filamentous actin (F-actin) and reveal the cytoarchitecture of cells within the explant. The labeled explants were examined by high resolution confocal microscopy (FIG. 4). G8$^{pos}$ cells were discovered localized in niches that were nestled among the lens epithelial cells (FIG. 4A). A typical niche of G8$^{pos}$ cells (shown at higher magnification in FIG. 4B, lower panel) contained, on average, 7 cells (7.57+/-0.66; Avg+/-SEM). Up to 14 such niches were detected in an epithelial explant. The positioning of the G8$^{pos}$ cell niches within the lens epithelium corresponded to the equatorial region of the intact lens. Previous studies show that G8$^{pos}$ cells often co-express mRNA for the myogenic transcription factor MyoD. Expression of MyoD mRNA by G8$^{pos}$ cells within the E15 lens epithelium was examined by double labeling the epithelial explants with G8 mAb tagged with fluorescein and with DNA dendrimers conjugated both to an anti-sense oligonucleotide sequence for MyoD mRNA and the fluorochrome Cy3 (Gerhart et al. (2000) J. Cell. Biol., 149:825-34; Gerhart et al. (2004) Biol. Proced. Online 6:149-156). Fluorescence imaging showed that the G8pos cells present within the lens epithelium also expressed MyoD mRNA (inset, FIG. 4A).

Orthogonal sections of Z-stacks collected by laser scanning confocal microscopy were created to investigate the microenvironment of the G8pos cell niches within the lens epithelium. The Z-stacks were acquired as one micron thick optical sections in an apical to basal direction in the region of the niche. Analysis of the orthogonal sections revealed that the niches of G8$^{pos}$ cells were localized along the apical surfaces of the lens epithelial cells, with little evidence of G8$^{pos}$ cells associated with the lens basement membrane (FIG. 4B, see arrow, top panel). The unique location of the G8$^{pos}$ cell niches positioned these cells such that they would be able to function as rapid responders to injury of the epithelium.

A central aspect of this study was to examine the response of G8$^{pos}$ precursor cells to injury of the lens epithelium. For these studies the lens epithelium was wounded by mock cataract surgery and placed in culture as ex vivo explants (FIG. 5A). The response of G8$^{pos}$ precursor cells to injury of the epithelium was determined after one hour in culture in media containing serum. At this time the cultures were fixed, immunostained with antibody to the G8 antigen, co-stained for F-actin and examined by confocal microscopy (FIG. 5B-F) Image analysis revealed that within this short time post-injury the G8$^{pos}$ precursor cells had emerged from their niches and their population size had expanded (FIG. 5B, C). In addition, G8$^{pos}$ cells had rapidly migrated to the wound edges (FIG. 5D-F), both the leading edge adjacent to where the fiber cells had been removed (FIG. 5D, E), and the cut edge where the epithelium had been flattened (FIG. 5F). An orthogonal section through Z-stacks collected by confocal imaging revealed that the G8$^{pos}$ cells traveled to the wound edges by migrating along the apical surfaces of the epithelium (FIG. 5E, arrow, top panel). The migrating G8$^{pos}$ cells exhibited a mesenchymal morphology, a phenotype confirmed by their expression of the mesenchymal marker vimentin (FIG. 5G-I). These results demonstrated that the subpopulation of G8$^{pos}$ mesenchymal precursor cells within the lens epithelium responded rapidly to injury of the epithelium by emerging from their niches, expanding, and migrating to the wound edges.

Throughout the wound healing process, which takes approximately three days, G8$^{pos}$ cells were found in clusters along the apical surfaces of the lens epithelium as well as at the wound edges. To investigate whether the G8$^{pos}$ cells that responded to epithelial wounding were indeed progeny of the G8$^{pos}$ cells present at time 0 (T0, immediately following microsurgery) G8$^{pos}$ cells were tagged at T0 with G8 antibody and a rhodamine-conjugated secondary antibody and tracked during the period of wound closure. At both 24 (FIG. 6A-F) and 72 (FIG. 6G-I) hours in culture the explants were fixed and the G8$^{pos}$ cells present at these times immunostained with the G8 mAb tagged with an Alexa Fluor 488-conjugated secondary antibody. Confocal analysis showed that during active wound healing (24 hours) all G8$^{pos}$/Alexa Fluor 488 labeled cells also labeled with the G8-rhodamine tag, whether the G8$^{pos}$ cells were located in clusters along the epithelium (FIG. 6A-C) or had migrated to the leading wound edge (FIG. 6D-F). Even as wound healing was completed (72 hours) all G8$^{pos}$/Alexa Fluor 488-labeled cells were co-labeled with the G8-rhodamine tag (FIG. 6G-I). These results demonstrated that the G8$^{pos}$ cells involved in the wound healing response of the lens epithelium were derived from the population of G8pos cells present at T0.

Healing of the wounded lens epithelium (wound closure) occurs before molecules associated with fibrosis, such as α smooth muscle actin (α-SMA) and fibronectin, are detected biochemically (Walker et al. (2007) Invest. Ophthalmol. Vis. Sci., 48:2214-23). However, within days after wound healing is complete expression of both of these molecules is induced. At this time, □-SMA positive cells with a mesenchymal morphology typical of emerging myofibroblasts appear among the lens epithelial cells (Walker et al. (2007) Invest. Ophthalmol. Vis. Sci., 48:2214-23). Now, using high resolution confocal imaging, it was investigated whether the G8$^{pos}$ cells that were activated in response to injury of the lens epithelium were the precursors of the myofibroblasts that appeared at later times in the ex vivo injury model. A myofibroblast is defined as a mesenchymal cell that has organized α-SMA into stress fibers (Tomasek et al. (2002) Nat. Rev. Mol. Cell. Biol., 3:349-63; Hinz et al. (2007) Am. J. Pathol., 170:1807-16), a feature that provides these cells with the contractile function that links them to fibrotic diseases like PCO. To examine whether G8$^{pos}$ cells were precursors of the myofibroblasts that emerge in the culture model, image analysis was performed on ex vivo explants that were cultured under serum free conditions, fixed on culture day 6, immunolabeled with the G8 mAb and a rhodamine-conjugated secondary antibody, and co-labeled with an α SMA antibody directly conjugated to fluorescein (FIG. 7 A-C). Confocal microscopy imaging revealed the presence of G8$^{pos}$ cells that contained α-SMA positive stress fibers, demonstrating that G8$^{pos}$ cells were indeed a source of myofibroblasts in this wound model. In addition, it was discovered that there was a progression from G8$^{pos}$ precursor cell to myofibroblast within small clusters of G8$^{pos}$ cells associated with the epithelium. The transitional cell types included G8$^{pos}$ cells with little to no expression of α SMA (white arrowhead), G8$^{pos}$ cells that expressed α SMA not yet organized into stress fibers (arrow), and G8$^{pos}$ cells containing α SMA positive stress fibers (open arrowhead), the G8 expressing myofibroblasts. This study also demonstrated that a final step in the differentiation of G8 cells to myofibroblasts was loss of the precursor cell antigen G8 (broken arrow). The loss of a precursor cell marker upon differentiation is a feature these cells share with the differentiated progeny of many precursor cell populations (Cattaneo et al. (1990) Nature 347:762-5; Bai et al. (2009) Neuroreport., 20:918-22).

Next it was examined whether it was possible to push the G8$^{pos}$ cells to differentiate into myofibroblasts. For these studies, the fact that myofibroblast development is known to be enhanced in rigid environments was used (Hinz, B. (2007) J. Invest. Dermatol., 127:526-37) and the ex vivo cultures were grown in serum containing media that permitted G8$^{pos}$ cells at the cut edge to migrate from the lens capsule onto the rigid culture dish. This population of G8$^{pos}$ cells was examined for expression of α SMA in G8$^{pos}$ cells at culture day 3, a time point before α-SMA positive myofibroblasts had emerged within their native microenvironment of the lens epithelium. The results demonstrated that the transition from G8$^{pos}$ precursor cells to α-SMA positive myofibroblasts was promoted when the G8$^{pos}$ cells came in contact with a rigid substrate (FIG. 7D-F). The process of transition from G8$^{pos}$ cell to myofibroblast was the same as described above for emergence of myofibroblasts on the lens capsule. These data demonstrate that G8$^{pos}$ cells give rise to myofibroblasts.

Lastly, it was examined whether α-SMA expression was suppressed in the ex vivo cultures when G8$^{pos}$ cells were eliminated on the first day in culture by labeling them with the G8 antibody and lysing them with complement. Cell lysis in the treated cultures was confirmed by trypan blue uptake, as this dye is excluded from live cells. Trypan blue staining was detected in small colonies of cells (FIG. 7G, G8+C, ablation, see encircled large colony at the leading edge). The distribution of the trypan blue labeled colonies resembled that of the expanded colonies of G8$^{pos}$ cells typically present at culture day 1. Twenty-four hours after ablation lysis was confirmed by the subsequent loss of cells from regions that had stained for trypan blue (FIG. 7G, G8+C, 1D post-ablation). Similar cell loss was not observed in control cultures incubated with complement alone (FIG. 7G, C). Following G8 cell ablation the ex vivo explants (ablated and controls) were cultured for six days, a time point by which untreated control cultures typically express α SMA, as shown here by immunoblot analysis (FIG. 7H, U). Expression of α SMA was suppressed when $G8^{pos}$ cells were ablated at culture day 1 (FIG. 7H, G8+C), while in cultures exposed to G8 antibody (G8) or complement alone (C) there was little effect on α SMA expression. These results confirm that $G8^{pos}$ cells are the precursors of myofibroblasts.

In this study, the discovery that a distinct subpopulation of mesenchymal precursor cells were present in niches localized among the cells of the lens epithelium is reported. This cell type rapidly responded to injury of the epithelium and had the potential to differentiate into myofibroblasts. Unique features of these cells included the expression of the cell surface antigen G8 and MyoD mRNA, characteristics they shared with a previously identified epiblast subpopulation that becomes incorporated into various embryonic tissues (Gerhart et al. (2001) J. Cell. Biol., 155:381-92), including ones that lack myogenic potential such as the lens. Following wounding of the lens epithelium the $G8^{pos}$ subpopulation emerged from their niches, expanded in population size, exhibited a mesenchymal phenotype and migrated to the wound edge. The presence of mesenchymal cells at the wound edge is a characteristic of many epithelial wound healing models, but their appearance is typically attributed to an EMT. The instant studies of the wounded lens epithelium suggested an alternate paradigm where $G8^{pos}/MyoD^{pos}$ precursor cells are the progenitors of the mesenchymal cells that responded to injury and localized to the wound edge. This same precursor population can differentiate into myofibroblasts, whose appearance following wounding is associated with the development of fibrotic disease. This finding was of particular importance to the development of the lens fibrotic disease PCO, a consequence of wounding of the lens epithelium during cataract surgery. However, the presence of small subpopulations of cells that express the G8 antigen and/or MyoD in other tissues prone to fibrosis such as the lung, liver and kidney (Gerhart et al. (2001) J. Cell. Biol., 155:381-92; Mayer et al. (1997) J. Cell. Biol., 139:1477-84), indicates that the ability of activated $G8^{pos}/MyoD^{pos}$ to differentiate into myofibroblasts contributes to the development of fibrosis in many tissues.

Example 3

The eye of an adult mouse was embedded in paraffin, sectioned and stained with hematoxylin and eosin FIG. 8A. The arrows indicate the areas shown at higher magnification in the fluorescence photomicrographs in FIGS. 8B and 8C. Cells near the equator of the lens are labeled with the G8 antibody (arrows in FIGS. 8B and 8C). Cell nuclei are stained with a dye. These results demonstrate that skeletal muscle stem cells are present in the lens of the adult mouse.

Rhabdomyosarcomas are tumors containing cells that resemble skeletal muscle cells (FIGS. 9A-9D). The G8 antibody also recognizes its antigen in cultures of human rhabdomyosarcoma cells. The rhabdomyosarcoma cells synthesize molecules that also are present in myofibroblasts, including the G8 antigen, alpha smooth muscle actin (SMA), myosin and MyoD protein. These results indicate that the G8 antibody can be used to detect myofibroblasts in the human lens.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of inhibiting lens fibrotic disease, said method comprising administering to the eye of a patient in need thereof a therapeutically effective amount of at least one skeletal muscle stem cell targeting molecule and at least one cytotoxic molecule,
wherein said at least one skeletal muscle stem cell targeting molecule is conjugated to said at least one cytotoxic molecule,
wherein said skeletal muscle stem cell is present in the lens, and
wherein said skeletal muscle stem cell targeting molecule is an antibody immunologically specific for a molecule selected from the group consisting of G8 antigen, syndecans, c-Met, CD34, and M-cadherin.

2. The method of claim 1, wherein said at least one skeletal muscle stem cell targeting molecule and at least one cytotoxic molecule are contained within a composition further comprising at least one pharmaceutically acceptable carrier.

3. The method of claim 1, wherein said lens fibrotic disease is posterior capsular opacification or anterior subcapsular opacification.

4. The method of claim 1, wherein said cytotoxic molecule is selected from group consisting of complement, heat sensitive carbon nanocrystals, cytotoxic antibiotics, cationic amphipathic lytic peptides, radionuclides, and toxins.

5. The method of claim 1, wherein said skeletal muscle stem cell targeting molecule and said cytotoxic molecule is administered directly to the lens or the surrounding tissue.

6. The method of claim 1, wherein said skeletal muscle stem cell targeting molecule is a G8 antibody.

7. The method of claim 4, wherein said cytotoxic molecule is complement.

8. The method of claim 1, wherein said skeletal muscle stem cell targeting molecule is an antibody which specifically binds a molecule selected from the group consisting of G8 antigen, syndecans, and c-Met.

9. The method of claim 1, wherein said at least one skeletal muscle stem cell targeting molecule and at least one cytotoxic molecule are administered intraocularly.

10. The method of claim 1, wherein said syndecans is syndecan-3 or syndecan-4.

11. The method for claim 1, wherein said skeletal muscle stem cell targeting molecule is an antibody immunologically specific for a molecule selected from the group consisting of syndecan-3, syndecan-4, and c-Met.

* * * * *